United States Patent [19]

Snyder et al.

[11] 4,312,950
[45] Jan. 26, 1982

[54] DISPOSABLE SWAB AND CULTURE UNIT

[75] Inventors: Thomas A. Snyder, Willow Grove; Walter T. Leible, Warminster, both of Pa.

[73] Assignee: Hillwood Corporation, Warminster, Pa.

[21] Appl. No.: 135,422

[22] Filed: Mar. 31, 1980

[51] Int. Cl.³ ............................................. C12M 1/30
[52] U.S. Cl. .................................. 435/295; 128/759; 401/183
[58] Field of Search ................. 128/759; 435/294, 295

[56] References Cited

U.S. PATENT DOCUMENTS

| | | | |
|---|---|---|---|
| 3,890,954 | 6/1975 | Greenspan | 435/295 |
| 4,014,746 | 3/1977 | Greenspan | 435/295 X |
| 4,014,748 | 3/1977 | Spinner et al. | 128/759 X |
| 4,184,483 | 1/1980 | Greenspan | 435/295 X |
| 4,223,093 | 9/1980 | Newman et al. | 435/294 X |

Primary Examiner—Robert J. Warden
Attorney, Agent, or Firm—Seidel, Gonda, Goldhammer & Panitch

[57] ABSTRACT

A two-piece telescoping cylinder made of a flexible plastic material forms a disposable container for a swab and a liquid culture medium. The upper piece serves as a handle for the swab and cooperates with the lower piece to form a sealed container for the swab and liquid. A generally conical plug having a base slightly larger than the inside diameter of the cylinder divides the lower piece into two compartments, sealing the liquid from the swab. When the telescoping parts are pushed together, the swab contacts the plug and pivots it in relation to the side walls of the tube so that the seal is broken and the liquid may saturate the swab or a cotton wad immediately above the swab.

5 Claims, 8 Drawing Figures

U.S. Patent     Jan. 26, 1982     4,312,950
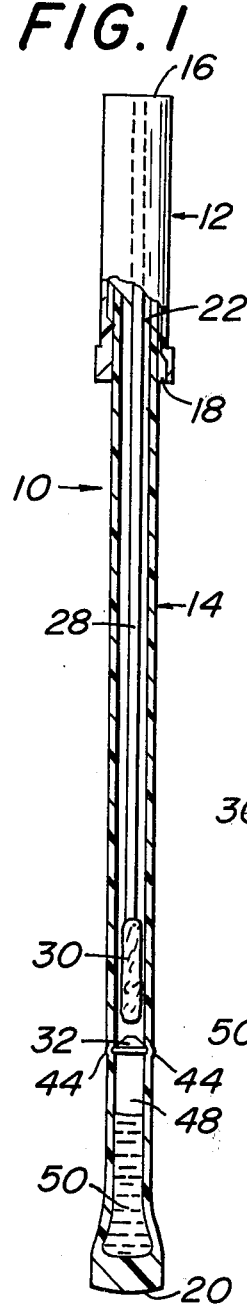
FIG. 1
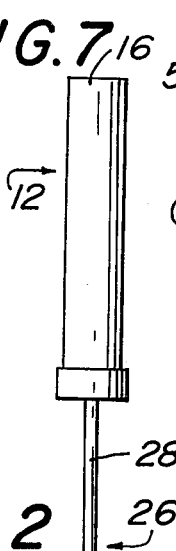
FIG. 7
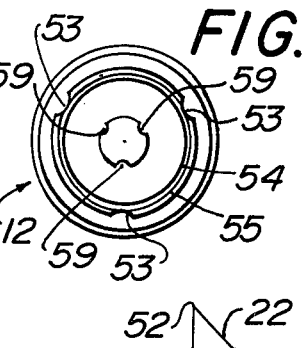
FIG. 8
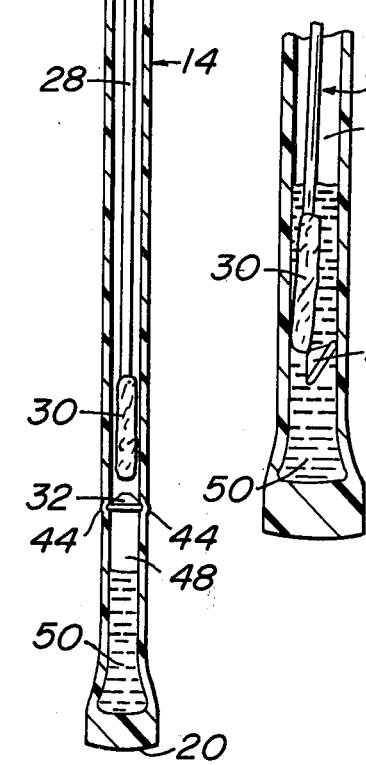
FIG. 2
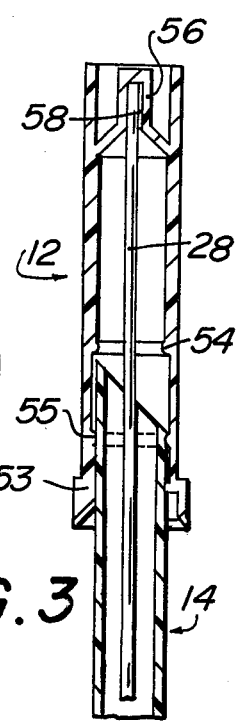
FIG. 3
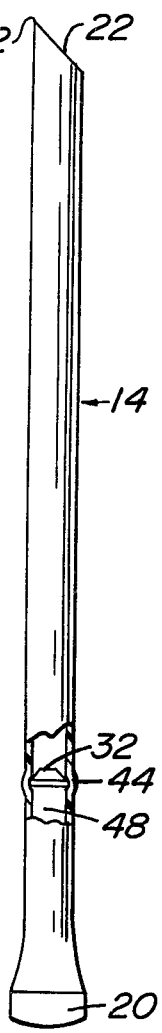
FIG. 4
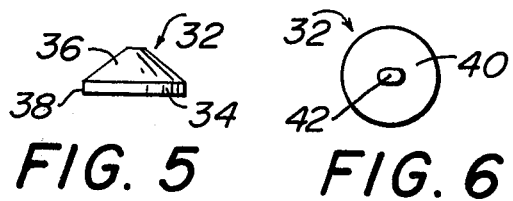
FIG. 5     FIG. 6

DISPOSABLE SWAB AND CULTURE UNIT

BACKGROUND OF THE INVENTION

This invention is related to our corresponding U.S. patent application Ser. No. 135,412 for a "Self-Contained Swab Unit" filed on the same day as this application.

In the classical taking of bacteria samples, a sterile absorbent swab or a tissue scraping blade is used to pick up bacteria by contact with the infected tissue. The swab or scraper is then placed in a culture medium to maintain the bacteria for future testing and examination.

In order to collect an accurate bacteria sampling, care must be taken to prevent the introduction of ambient bacteria from a source other than the tissue under investigation. Thus, the swab must be maintained in a sterile environment until it is applied to the infected tissue and must be immediately returned to a sterile environment thereafter while it is being transported to the culture medium.

In response to inherent difficulties in maintaining this overall sterile environment, the modern trend has favored self-contained units wherein the swab and culture medium are both carried in a sealed disposable tube. Just prior to tissue sampling, the seal is broken and the swab removed for use.

Immediately after tissue sampling, the swab is replaced in the unit and the unit is resealed. An internal seal holding the swab and culture medium separate in storage is ruptured or otherwise displaced, allowing the medium to contact the bacteria bearing swab, thus beginning the culture process.

The advantages of the modern method are readily apparent. The self-contained unit carries its own sterile environment, eliminating the previous necessity of maintaining a large scale sterile environment in the storage facility for the swabs and culture medium and during incubation. Thus, the unit can be carried and stored in a doctor's bag or in a technician's portable kit until it is needed, and once used will maintain the integrity of the sample in a sterile environment while being transported to the lab.

OBJECT OF THE INVENTION

An object of the present invention is to provide an improved self-contained unit of the type described above. Specifically, it is desired to provide an improved means of maintaining a rupturable seal between the swab and culture medium. Ideally, such a seal would be air and watertight even when the unit is subjected to minor blows, such as would occur in a doctor's bag or a technicians's kit, and when placed under a modest weight, such as other medical instruments being stored on top of it. Yet the seal should rupture easily and completely when the bacteria-bearing swab is pushed through it, so that the swab may come into contact with the entire contents of the medium section.

Since the units are intended to be disposable, the cost factor is important. A seal that meets the operational requirements of the previous paragraph must also be capable of being installed in the unit inexpensively. This will almost invariably necessitate that the seal be installed by a simple automated process.

It is toward these dual objects, an improved seal at a reasonable cost, that the present invention is directed.

SUMMARY OF THE INVENTION

A disposable swab and culture unit is made in the form of a two-piece telescoping cylinder. The two pieces are themselves cylinders, open at one end and closed at the other. When the open end of one is inserted into the open end of the other, an airtight closed cylinder is formed. Inside the cavity of the cylinder is inserted a conical plug large enough in diameter to divide the cavity into two isolated compartments. In one compartment is provided a liquid culture medium; in the other a swab or tissue scraping blade. The swab or scraper is attached to one of the two cylinder pieces, which acts as a handle thereto.

When the two pieces are pushed together to rupture the seal, the swab or scraper tip comes in contact with the conical plug and moves along the conical surface toward the inner walls of the unit. This causes the force of the tip to be concentrated near the perimeter of the plug, so that the plug will pivot and break the seal between the plug and the walls of the unit.

The unit may also be used on a self-contained swab. The swab is mounted on an extremity of the cylinder, and the conical plug seals the liquid away from the swab. When the plug is pivoted, the liquid can saturate the swab for immediate use.

BRIEF DESCRIPTION OF THE DRAWINGS

For the purpose of illustrating the invention, there shown in the drawings a form which is presently preferred; it being understood, however, that this invention is not limited to the precise arrangements and instrumentalities shown.

FIG. 1 is a longitudinal sectional view of a swab and culture unit according to one embodiment of the present invention;

FIG. 2 illustrates the lower portion of FIG. 1 on an enlarged scale and shows the components after the seal has been broken;

FIG. 3 is an elevation view of the upper portion of the device;

FIG. 4 is an elevation view of the lower portion of the device with a section window showing the plug;

FIG. 5 is a side view of the plug;

FIG. 6 is a bottom view of the plug.

FIG. 7 illustrates the upper portion of the unit as a handle for the swab.

FIG. 8 is a front end view of the upper portion of the unit.

DETAILED DESCRIPTION OF THE DISCLOSURE

Referring to the drawings in detail wherein like numerals indicate like elements, the present invention is embodied in a disposable swab and culture unit designated generally as 10. The unit 10 is composed of two major sub-assemblies, namely an upper portion 12 and a lower portion 14. The upper portion 12 is a preferably a cylindrical plastic tube closed at one end 16 and open at the other end 18. The lower portion 14 is preferably a cylindrical plastic tube closed at one end 20 and open at the other end 22. Tube 14 is preferably an extruded tube made of a plastic such as polypropylene or a copolymer blend selected to preserve the integrity of the seal chamber. Tube 12 is preferably of the same material but is formed by injection molding.

In the preferred embodiment shown, portions 12 and 14 are telescopically disposed. Thus, upper portion 12 slides over lower portion 14 in the manner of a male-female junction. Upper portion 12 has an inside diameter minutely smaller than the outside diameter of lower portion 14 so that lower portion 14 can be inserted into upper portion 12 to provide a sealed unit 10 with a sliding seal where the upper and lower portions come in contact. A swab 26 is provided in upper portion 12. Swab 26 may be any commonly available swab having a shaft 28 and an absorbent tip 30 of any absorbent material, such as cotton or rayon. Additionally, a scalpel or tissue scraper tip could be substituted where such instruments are more appropriate for collecting specimens. Hereinafter, reference shall be made only to the swab tip, it being understood that the ready substitution of a scalpel or scraper is implied.

Lower portion 14 contains a generally conical plug 32 having a base portion 34 and a cone portion 36. The base portion 34 has a cylindrical surface defined along its outside diameter that will be referred to as the sides 38 of the base 34. A generally flat surface 40 is provided by the bottom of the base 34. Surface 40 contains a centering depression 42, shown as a rectangular depression in these drawings, so that a centering tool may be used to place the plug 32 within the container. Plug 32 may be inserted into portion 14 through the adjacent end 20 before end 20 is sealed. The plug 32 is preferably integrally formed by injection molding.

The outside diameter of base 34 is slightly larger than the inside diameter of lower portion 14. When plug 32 is inserted into lower portion 14 and properly centered, the generally flat surface 40 is perpendicular to the wall of the lower portion 14. Lower portion 14 is preferably composed of a sufficiently pliable material such as a copolymer blend or polypropylene. In this manner, the wall of portion 14 will bulge outwardly as shown at 44 to accommodate the sides 38, thus causing a sealed cavity 48 in lower portion 14 which will serve as a reservoir for the liquid culture medium 50. Medium 50 can be loaded to a pre-determined amount before cavity 48 is sealed by a heating and crimping process to effect a seal at end 20. While the heating and crimping process is preferred, any means of sealing would suffice.

Referring now to FIG. 4, the open end of the lower portion 14 is cut on a bias, producing a sharpened tip 52 to facilitate insertion of portion 14 into the open end 18 of the upper portion 12.

Referring now to FIGS. 3 and 8, there are three raised rails 53 at the opening of the bore of upper portion 12 to guide in and center lower portion 14. Rails 53 terminate in an annular lip 55 which reduces the bore diameter of portion 12 to slightly less than the outside diameter of lower portion 14. Lip 55 acts as a seal for the unit to keep outside contaminents from coming in contact with the swab and the inside walls of the unit. The unit can be assembled in a sterile atmosphere. When portions 12 and 14 are fit together in assembly, lip 55 forms a tight seal to maintain a sterile interior during storage and transportation prior to use.

The bore of upper portion 12 has a second annular lip 54 which projects radially inwardly to reduce the bore diameter of portion 12 at lip 54 to significantly less than the outside diameter of lower portion 14. Lip 54 acts as an interference stop to prevent lower portion 14 from being inserted completely into upper portion 12 without a conscious effort. It should be noted that lip 54 is located at a position whereby swab tip 30 is spaced from plug 32. A conscious force must be used to push the two portions together to cause lower portion 14 to move past lip 54 and further into upper portion 12.

Lip 54 also acts as a seal after the unit has been used. When a bacteria sample has been obtained on the swab, upper portion 12 is inserted over lower portion 14 and a conscious force is applied to force portion 14 past lip 54. Since portion 14 has a larger diameter than upper portion 12 above lip 54, an extremely tight seal is formed. This prevents contamination of the sample and from the sample to the outside environment.

Again, referring to FIGS. 3 and 8, there is integrally formed within upper portion 12 a smaller cylindrical shaft 56 with a hollow cavity 58. Cavity 58 has an inside diameter at its lowermost end which is slightly larger than the outside diameter of swab shaft 28 and tapers a diameter smaller than shaft 28. There are also provided three small flexible nipples 59 inside shaft 56 to grasp and hold the swab shaft 28. When swab shaft 28 is inserted into hollow cavity 58, shaft 28 will be held firmly in place. This relationship of cavity 58 and shaft 28 allows the user to employ upper portion 12 as a handle to the swab 26 as shown in FIG. 7. When taking a culture sample, the user need not ever touch a surface that would be on the inside of the sealed unit 10.

In practice, the unit 10 is used as follows. The unit 10 when stored prior to use is in the configuration shown in FIG. 1. The swab 26 and the liquid culture medium 50 are isolated by plug 32. When it is desired to take a bacteria sample, the user pulls upper portion 12 away from lower portion 14, thereby withdrawing the swab 26. While using the upper portion 12 as a handle, the user rubs the absorbent tip 30 of the swab 26 over the infected tissue area, thereby picking up a bacteria sample on the absorbent tip 30. The user then re-inserts the swab 26 into lower portion 14 and slides the upper portion 12 and the lower portion 14 together. The sharpened tip 52 provides for ease of insertion. When the lower portion 14 encounters lip 54, the increased frictional force must be overcome by a conscious push on the user's part. When the user pushes the lower portion 14 past the lip 54, the tip 30 of the swab 26 comes into contact with the cone-shaped portion 36 of plug 32. The conical shape guides the swab tip 30 radially outward on the plug 32, so that pressure is exerted to force the plug 32 to pivot from a centered position as shown in FIG. 2, thus allowing the liquid culture medium 50 to freely contact the absorbent tip 30 and the bacteria sample thereon.

Thus, it is apparent that an improved swab and culture unit is provided consistent with the objects of the invention. The conical plug cooperates with the inner walls of the unit to provide a tight seal. The seal is not easily ruptured by minor jolts or weights placed on the unit. Moreover, the frictional stop provided by the shoulder in the upper portion makes it unlikely that the seal will be ruptured by an accidental telescoping together of the pieces. It will also be observed that when the seal is intentionally ruptured, the entire contents of the culture may freely come in contact with the swab tip. Finally, it will be noted that the plug itself is of an inexpensive design and is capable of being inserted easily and by automated means into the unit.

The present invention may be embodied in other specific means without departing from the spirit or essential attributes thereof and, accordingly, reference should be made to the appended claims, rather than to the foregoing specification, as indicating the scope of the invention.

I claim:

1. A disposable swab and culture unit comprising:
   (a) a generally hollow cylinder having a closed end and and open end capped by a cap placed in sliding telescoping contact over said cylinder;
   (b) a swab comprising a shaft with a specimen collecting tip at one end, the other end of the shaft being attached to interior of the cap in such a manner that the swab is disposed inside the cylinder and may be moved along the axis of the cylinder by the telescoping movement of the cap;
   (c) a liquid culture medium within the cylinder;
   (d) a conical plug having a base portion slightly larger than the diameter of the bore of the cylinder, the plug being inserted within the bore of said cylinder with the conical face thereof facing the specimen collecting tip of the swab to form a sealed chamber in the portion of said cylinder between the closed end and the plug for containing the liquid culture medium, said plug being pivotable, by contact of the specimen collecting tip of the swab against the conical face of the plug when the cap is moved in sliding telescoping contact over the cylinder, to a position where it no longer forms a sealed chamber.

2. A disposable swab unit as in claim 1, wherein the cap has an integral cylindrical cavity having an inside diameter tapering to be smaller than the outside diameter of the swab shaft, the swab shaft being inserted into said cavity and held there by contact so that the cap may be used as a handle for the swab.

3. A disposable swab and culture unit, comprising:
   (a) a closed telescoping cylinder having first and second portions, each portion being a cylindrical tube open at one end and closed at the other end, the open end of one portion being inserted into the open end of the other portion to form the closed telescoping cylinder, and said portions being separable from each other;
   (b) a swab having a shaft and a specimen collecting tip, said shaft being attached to the first portion of said telescoping cylinder in such manner that the swab is disposed inside of the cylinder when the first and second portions are together, and said first portion may be used as a handle for the swab when the portions are separated;
   (c) a conical plug having a base whose outside diameter is slightly larger than the inside diameter of the second portion of the telescoping cylinder, said plug being positioned inside said second portion with the conical face of said plug directed toward swab tip, said plug thereby dividing the second portion into two separate compartments, and said plug being movable to a position where it no longer separates said compartments by contact with the swab tip when the first and second portions of the telescoping cylinder are pushed together in sliding telescoping contact; and
   (d) a liquid culture medium in the compartment defined by the base of the plug and the closed end of the second portion of the telescoping cylinder.

4. A disposable swab and culture unit as in claim 3, the first portion having on its inner surface at least one annular lip wherein the inner diameter of the first portion is reduced in order to form an interference fit and a seal around the outer surface of the second portion.

5. A disposable swab and culture unit as in claim 3, the first portion having on its inner surface two spaced annular lips, the first lip reducing the inner diameter of the first portion to form a seal around the outer surface of the second portion at assembly, and the second lip located further from the open end of the first portion and further reducing the inner diameter of the first portion to form an interference stop at assembly and a seal around the outer surface of the second portion after the swab has been used.

* * * * *